United States Patent
Shih

(10) Patent No.: US 9,547,099 B2
(45) Date of Patent: Jan. 17, 2017

(54) MAGNETIC INDUCTION PAD

(71) Applicant: CAREMED SUPPLY INC., New Taipei (TW)

(72) Inventor: Pao Ming Shih, Taipei (TW)

(73) Assignee: CAREMED SUPPLY INC., New Taipei (TW)

( * ) Notice: Subject to any disclaimer, the term of this patent is extended or adjusted under 35 U.S.C. 154(b) by 122 days.

(21) Appl. No.: 14/605,532

(22) Filed: Jan. 26, 2015

(65) Prior Publication Data

US 2016/0216394 A1   Jul. 28, 2016

(51) Int. Cl.

| | |
|---|---|
| *G01B 7/14* | (2006.01) |
| *G01V 3/10* | (2006.01) |
| *G01D 5/20* | (2006.01) |
| *A61B 5/11* | (2006.01) |

(52) U.S. Cl.
CPC ............... *G01V 3/10* (2013.01); *A61B 5/1116* (2013.01); *A61B 5/1126* (2013.01); *G01D 5/2006* (2013.01)

(58) Field of Classification Search
USPC ............... 324/207.11, 207.15, 207.17; 5/713
See application file for complete search history.

(56) References Cited

U.S. PATENT DOCUMENTS 8,664,942 B2 *   3/2014  May .................. F16F 9/04
                                                    324/207.15

* cited by examiner

*Primary Examiner* — Minh Phan
(74) *Attorney, Agent, or Firm* — Rabin & Berdo, P.C.

(57) ABSTRACT

The present invention provides a magnetic induction pad. The magnetic induction pad includes a deformation body and a plurality of magnetic induction modules. The interior of the deformation body includes a filling space that is in connection with the outside via at least one gas nozzle. The external of the deformation body includes a first surface and a second surface. The first surface and the second surface include a plurality of first bag bodies and a plurality of second bag bodies, respectively. The plurality of first bag bodies are mutually arranged to form a first pattern. The plurality of second bag bodies are mutually arranged to form a second pattern that are the same as the first patterns, so as to enable the position of each of the plurality of first bag bodies on the first surface to have a corresponding arrangement to each of the plurality of second bag bodies of the second surface. The plurality of magnetic induction modules includes a group of magnetic members and a group of induction members. The group of magnetic members and the group of induction members are respectively arranged at the corresponding positions within the plurality of first bag bodies and the plurality of second bag bodies. According to the magnetic theory, it enables the determination of whether a human body lies down on a bed, on the basis of the degree of compression of the magnetic induction pad between the plurality of magnetic induction modules.

11 Claims, 10 Drawing Sheets

MAGNETIC INDUCTION PAD

FIELD OF THE INVENTION

The present invention relates generally to a magnetic induction pad, and more particularly, the present invention relates to a magnetic induction pad that is placed between a bed frame and a bed; in other words, it is for determining whether a human body has lain down on a bed based on the magnetism between the magnetic elements.

BACKGROUND OF THE INVENTION

For the majority of patients, including the patients with reduced mobility, those with physical disabilities or the elderly, resting in bed is a must in order for their health to be nursed back. Since these patients need to rest in bed for long periods of time, as such, surveillance cameras and surveillance equipment have often been set up by a lot of care centers, rehabilitation centers and hospitals, in order to ensure that the patient is still resting on the bed at specific times of the day. In addition, the surveillance cameras and surveillance equipment are also set up to help determine whether the patient has fallen off the bed after turning, or to help determine if the patient has left the bed. However, the presence of surveillance cameras can often make the person being monitored to feel uncomfortable, or even feel psychological pressure and as such is unable to have proper rest. Moreover, there may also be the concern that the privacy of the person being monitored may be violated.

Following changes in time and space, much progress has been made in the development of human technologies and also in the medical industries. With the maturation of these technologies, the traditional cameras that are used for monitoring whether a person is still resting on the bed are sufficiently replaced by various inventions, and moreover, these inventions may be installed in the interior of the bed, or may be installed to be in connection with the bed. For example, the weight sensing device may be installed in the four corners of the bed, or may be installed under the bed, such that it is in connection with the wheels. This arrangement enables the surveillance equipment to be connected to the structure of the bed from the outside.

However, although the aforesaid inventions of installing the surveillance cameras elsewhere such that the camera is not directed at the person being monitored may have prevented the problem of the person having psychological discomfort caused by the surveillance camera being directed at the person. However, using the method of the weight sensing device also has the problem of having a large margin of error and low sensitivity of detection, which may be caused by local compressions resulting from the person lying down or sitting on the bed.

SUMMARY OF THE INVENTION

The main objective of the present invention is to provide a magnetic induction pad that has a group of magnetic members, and data on the extent of the compression received by the magnetic induction pad may be obtained, by means of the group of magnetic members that is embedded within the magnetic induction pad for sensing the strength of compression, so as to determine whether a human body is lying on the bed.

The other objective of the present invention is to design the group of magnetic members in a manner such that it may be detached as well as being assembled; the group of magnetic members may be respectively assembled at the corresponding upper and lower surfaces of the magnetic induction pad. In addition, a number of positioning spaces may have been designed on the surface of the magnetic induction pad of the present invention, in order to house the group of magnetic members. The design of the present invention may also enable the quantities of the group of magnetic members assembled to be changed, and also enabling the distribution positions of the group of magnetic members on the surface of magnetic induction pad to be changed, and at the same time enabling accurate detection of whether the human body is still lying on the bed while using the minimum amounts of the group of magnetic members. In addition, the present invention also enables (adjustable) detection of magnetic strength to be achieved and brings about an accurate detecting effect.

In order to achieve the aforesaid objective, the magnetic induction pad for sensing an object on the bed of the present invention includes a deformation body and a plurality of magnetic induction modules, whereby the interior of the deformation body may include a filling space that changes the volume and size of the deformation body; whereby the filling space may be in connection with the outside via at least one gas nozzle, the external of the deformation body may include a first surface and a second surface; the first surface may include a plurality of first bag bodies, and the second surface may include a plurality of second bag bodies; the plurality of first bag bodies may be mutually arranged to form a first pattern, and the plurality of second bag bodies may be mutually arranged to form a second pattern that is the same as the first pattern, so as to enable the position of each of the plurality of first bag bodies on the first surface to have a corresponding arrangement to each of the plurality of second bag bodies of the second surface.

In accordance with an preferred exemplary embodiment of the present invention, the plurality of magnetic induction modules may include a group of magnetic members and a group of induction members, the group of magnetic members and the group of induction members may be respectively arranged at the corresponding positions within the plurality of first bag bodies and the plurality of second bag bodies, and whereby the group of magnetic members and the group of induction members may be used for sensing any changes in the distance of the first surface relative to the second surface.

In addition, the first surface and the second surface may further include a plurality of joint lines that are mutually parallel, so as to enable the filling space to form a plurality of channels, and there is conduction between the plurality of channels.

In accordance with a preferred exemplary embodiment of the present invention, the filling space may include a plurality of first channels that are parallel, adjacent and in connection with each other.

Moreover, in accordance with a preferred exemplary embodiment of the present invention, the filling space may include a first space and a second space that are not in connection with each other; the first space may include a plurality of second channels that are parallel to each other, and the plurality of second channels may be in connection with each other via a terminal regions; a third space may include a plurality of third channels that are parallel to each other, and the plurality of third channels may be in connection with each other via the terminal regions; and the plurality of second channels and the plurality of third channels may have a sequential alternating arrangement.

In order to prevent the occurrence of lack of continuous connection of parts of the channels of the magnetic induction pad of the present invention, which may be caused by the formation of recesses that occur as a result of compression of parts of the magnetic induction pad, the edge position of the deformation body may include at least one strengthening piece, so as to enable the edge region and the central region of the deformation body to respectively produce deformations in different directions when the deformation body is being compressed.

In addition, the strengthening piece may include a first anti-fold section and a second anti-fold section, whereby the first anti-fold section may be parallel to the edge position, and whereby the second anti-fold section may be perpendicular to the first anti-fold section.

The magnetic induction module may further include a processor, whereby the processor may be in electrical connection with the group of induction members and a fluid delivery device; the fluid delivery device may be in connection with the gas nozzle of the deformation body, and whereby the fluid delivery device may selectively input a filling material to the filling space of the deformation body, in order to change the volume of the filling space.

In other words, the magnetic induction pad of the present invention may be able to determine whether a human body is lying on the bed, no matter whether the person is in a sitting position in bed or has lied down on the bed, by means of the design that the positions of the outer surface of the first sheet body and the second sheet body correspond to the plurality of magnetic induction modules. This alignment of the first sheet bodies and the second sheet bodies and the plurality of magnetic induction modules may enable the sensing as well as detection of a reduction in the filling space that occurs as a result of a change in the deformation distance.

The two sides of the edge of the magnetic induction pad may further include a positioning device, and whereby the positioning device may include a plurality of positioning belts that are in connection with the outer edge of the deformation body, and whereby the positioning belt may include a group connection member. In accordance with a preferred exemplary embodiment of the present invention, the connection member may include a male connection member and a female connection member, whereby the female connection member may be adjacent to the male connection member; the male connection member may be in connection with the female connection member, and the male connection member and the female connection member may surround the positioning belt to form a positioning space that enables the bed to be fixed.

In accordance with a preferred exemplary embodiment of the present invention, the magnetic induction pad may further include a coated piece, whereby the coated piece may include a coated body that forms a cover space, and an extension member may be formed by the coated body extending outwards. The cover space may be used for covering the wide area of the deformation body, and whereby the extension member may include an acceleration sensing device.

In accordance with a preferred exemplary embodiment of the present invention, the coated body includes a first cover member that covers the first surface, a second cover member that covers the second surface and a third cover member that is in connection with the first cover member and the second cover member; the extension member is integrally connected with the third cover member.

As such, it is clear from the above that the distinguishing technical feature of the present invention is to enable the determination of whether a human body is still lying on the bed, or whether the person has escaped from, or has fallen off the bed, by means of the plurality of magnetic induction modules that correspond to the outer surface on the two sides of the deformation body sensing and detecting the deformation distance that is produced by the deformation body subsequent to compression of the deformation body. In addition to this, the design of the plurality of magnetic induction modules may be achieved through the bag body being positioned at positions that correspond to the two sides of the deformation body. Furthermore, the plurality of magnetic induction modules may also have the characteristic of being easily detachable, and as such, the plurality of the magnetic induction modules assembled as well as the relative positions of the plurality of magnetic induction modules may be arbitrarily changed, in order to enable the detection intensity to be adjusted while using the minimum number of magnetic induction modules to carry out accurate detection.

BRIEF DESCRIPTION OF THE DRAWINGS

The present invention can be understood in more detail by reading the subsequent detailed description in conjunction with the examples and preferred exemplary embodiments made to the accompanying drawings, wherein.

DETAILED DESCRIPTION OF THE PREFERRED EMBODIMENT

The accompanying drawings are included to provide a further understanding of the invention, and are incorporated in and constitute a part of this specification. The drawings illustrate the preferred exemplary embodiments of the invention and, together with the description, serve to explain the principles of the invention.

Figure 1:
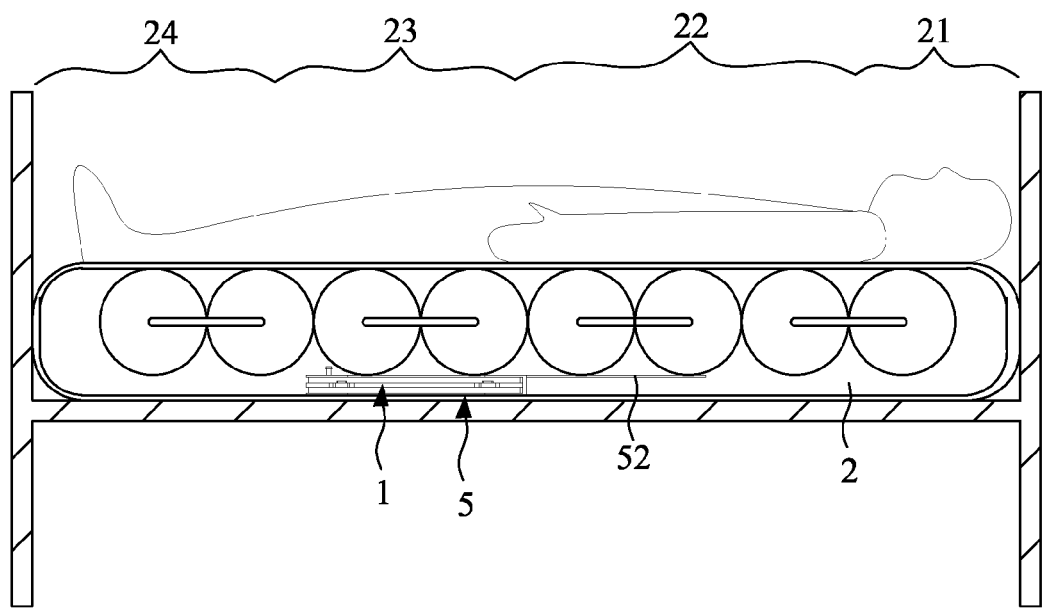
FIG. 1 is a cross-sectional schematic diagram showing a magnetic induction pad that is placed in between a bed frame and a bed for sensing a human body on the bed in accordance with a preferred exemplary embodiment of the present invention.
Figure 2:
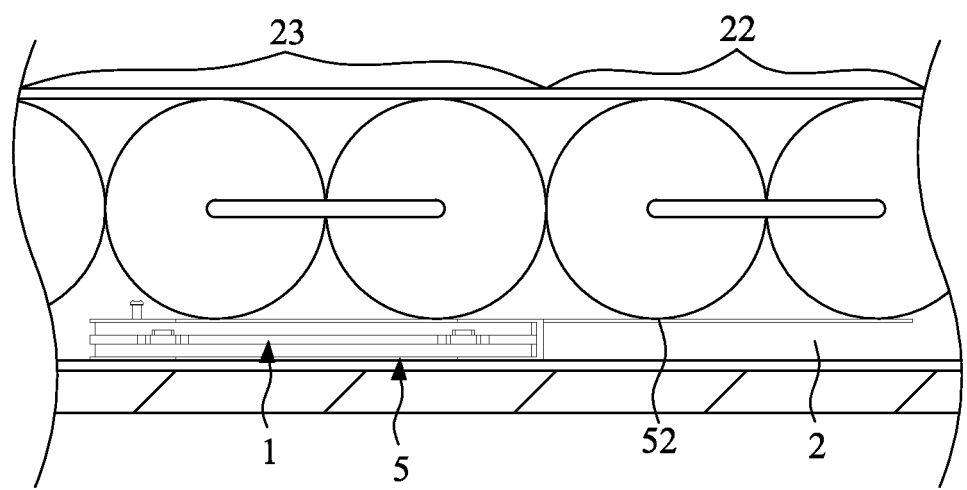
FIG. 2 is a partially enlarged schematic diagram illustrating the magnetic induction pad in accordance with a preferred exemplary embodiment of the present invention.

As shown in FIG. 1 and FIG. 2, the magnetic induction pad 1 of the present invention may be set up in between the frame of a bed and a bed body 2, whereby the bed body 2 may include a head part area 21, an upper body area 22 that is in continuous connection with the head part area 21, a buttock part area 23 that is in continuous connection with the upper body area 22, and a lower body area 24 that is in continuous connection with the buttock part area 23. It is clear from FIG. 1 that, and in accordance with a preferred exemplary embodiment of the present invention, the magnetic induction pad 1 of the present invention may be set up in between the frame of the bed and the buttock part area 23 of the bed body 2.

To be more precise, and in accordance with a preferred exemplary embodiment of the present invention, the bed body 2 may be made up of a plurality of interconnected conductive air bags. The phenomenon of a change of shape occurs when the bed body 2 is compressed by a weight, and when the human body is lying down on the bed body 2. Although the lying down position and sitting position are practically different, the state of compression of the air bags and the deformation states will also be different. However, under the majority of usage conditions, the central region of the bed body 2 may compressed. As such, the magnetic induction pad 1 of the present invention may be set up in the buttock part area 23 of the bed body 2 in order to achieve very good detection effects while using the minimum amount of the group of magnetic members.

It is clear from the drawings that the magnetic induction pad 1 of the present invention is configured to be placed below a plurality of air bags and also in the interior of the bed body 2. As such, while the person is lying down on the bed body 2 to enable the detection and sensing of the deformation distance that is brought about by a change in shape of the deformation body 3, caused by the weight of the human body on the bed, the person would not feel the presence of the magnetic induction pad of the present invention, nor would the presence of a foreign body be sensed.

Figure 3:
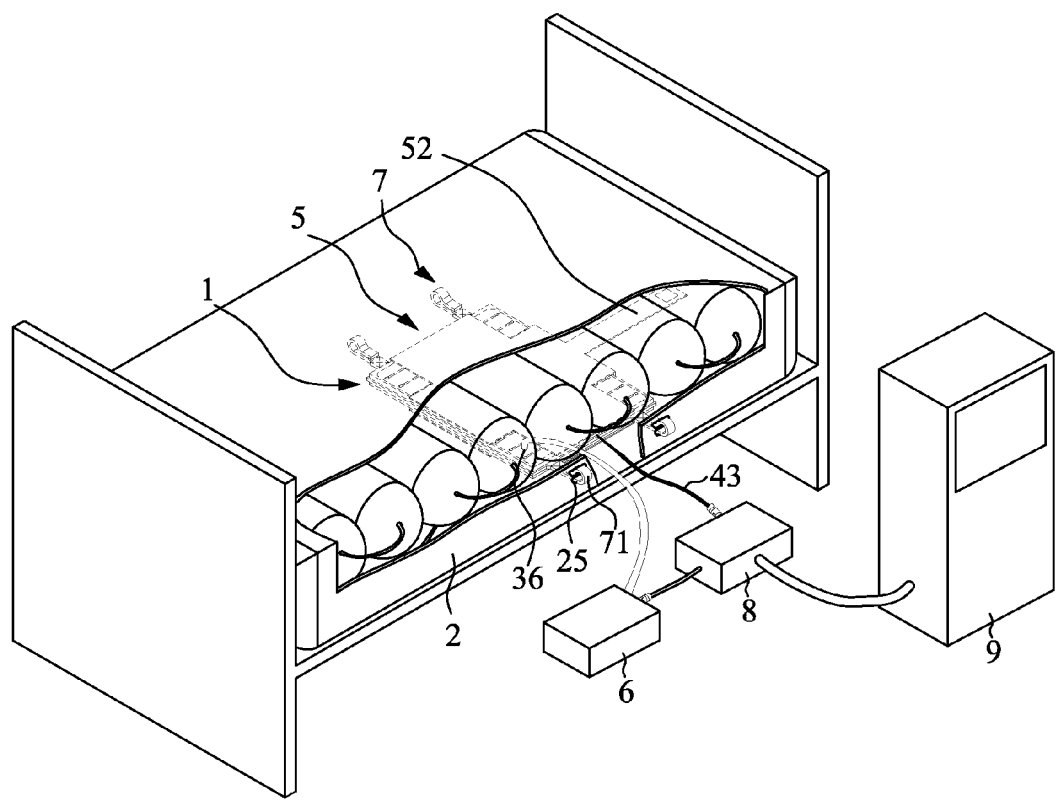
FIG. 3 is a three-dimensional schematic diagram illustrating the magnetic induction pad that is in connection with a plurality of magnetic induction modules and a processor via cables in accordance with a preferred exemplary embodiment of the present invention.

As shown in FIG. 3, the magnetic induction pad 1 of the present invention 1 may be mainly made up of three parts that include a deformation body 3, a plurality of magnetic induction modules 4 and a coated piece 5. Through being in connection with the fluid delivery device 6, the deformation body 3 may be filled with a gas, a fluid or a gelatinous substance, to enable the volume of the deformation body 3 as well as the relative distances above and below the deformation body 3 to be increased. Subsequent to the compression of and also a change in shape of the deformation body 3, the sensing of the relative numerical values of voltage and current of different strengths may be performed by the plurality of magnetic induction modules 4 that are located on the surface of the two sides of the deformation body 3. In other words, the plurality of magnetic induction modules 4 may be configured to be located in the area where compression takes place.

Moreover, subsequent to analysis of numerical values by a processor 8 which is in electrical connection with the plurality of magnetic induction modules 4, the results obtained indicating whether the human body is still in the bed body 2 is transmitted. This may be followed by the transmission of a warning noise, a warning smell and a warning light by the warning device 9 that is in electrical connection with the processor 8. The warning device 9 may also be configured to be an information display device having a monitor, and the information of whether the person is still on the bed body 2 is shown by the information display device. The presence of the information display device also enables the remote monitoring of whether the person has turned over or fallen off the bed body 2, this is such that feelings of anxiety and psychological discomfort by patients, those with reduced mobility, patients with physical disabilities or the elderly may be prevented.

When the voltage or current that is produced by the plurality of magnetic induction modules 4 is larger than a specific numerical value, this may then enable the determination of whether there is compression of the deformation body 3, brought about by the weight of the human body. The compression of the deformation body 3 causes the deformation distance produced by the deformation body 3 to exceed a numeral value that is originally anticipated or set, and also causes the plurality of magnetic induction modules 4 that are in relative positions of being above and below each other to be in contact with one another. The fluid that is inside the deformation body 3 is not able to bear the weight of the person, at this particular time point, the information is being transmitted to the processor 8 by the plurality of magnetic induction modules 4, and the processor 8 therefore transmits an order for the fluid delivery device 6 to refill fluid into the deformation body 3.

Figure 4:
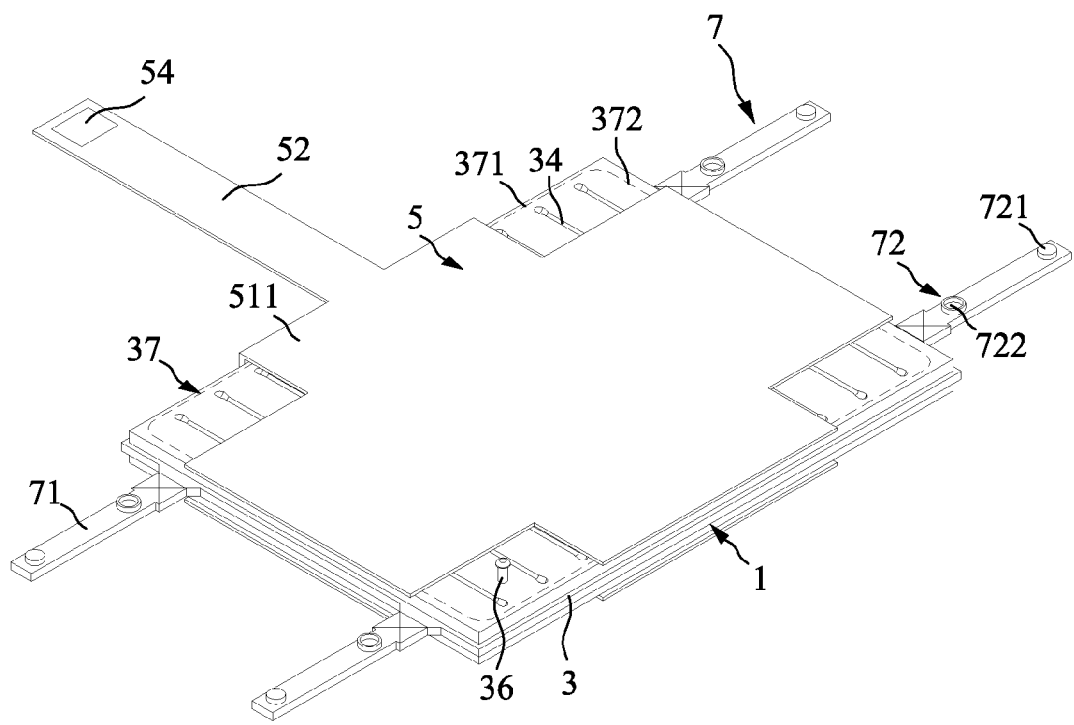
FIG. 4 is a three-dimensional schematic diagram illustrating the magnetic induction pad in accordance with a preferred exemplary embodiment of the present invention.
Figure 5:
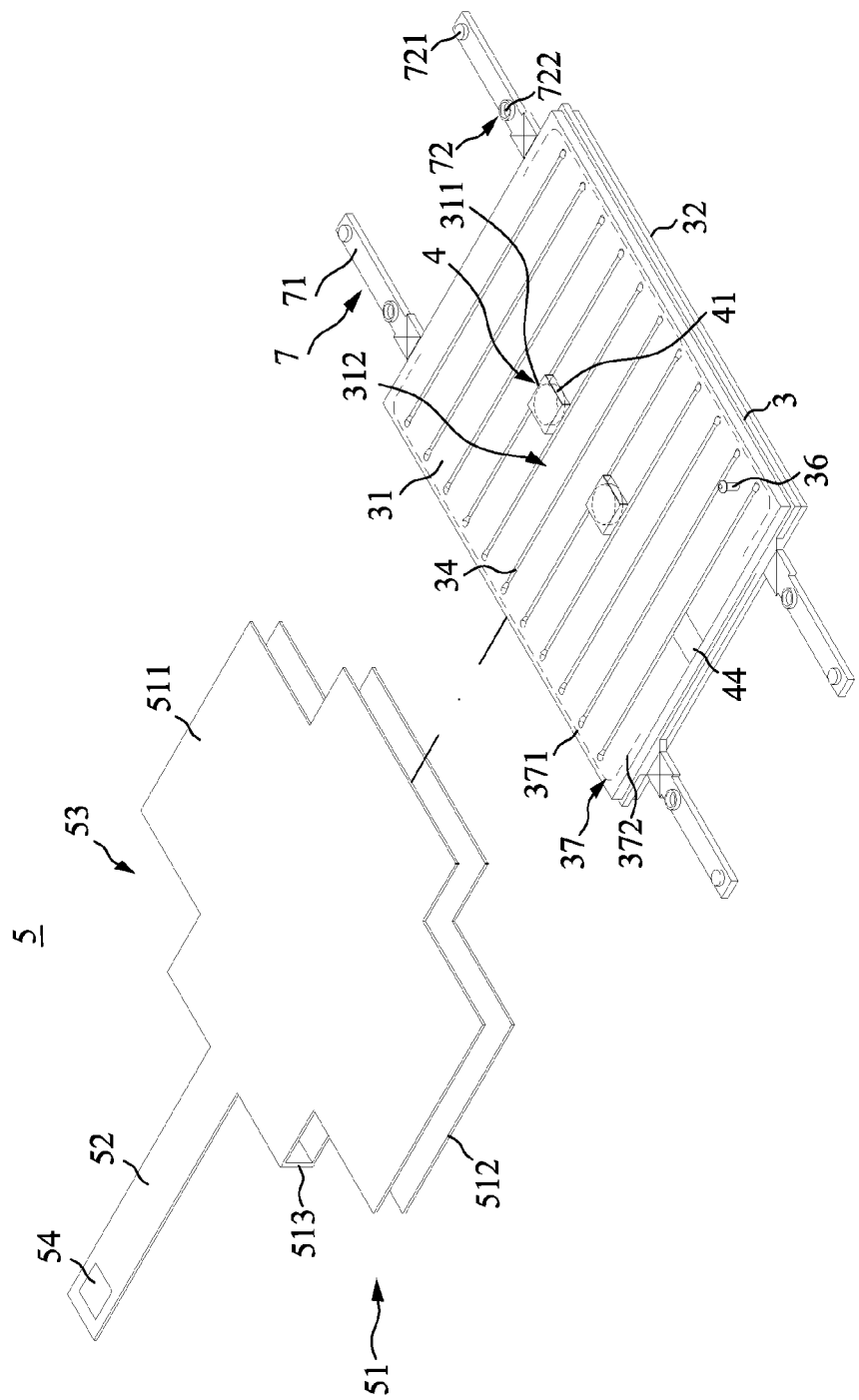
FIG. 5 is a partially exploded three-dimensional schematic diagram illustrating the magnetic induction pad of FIG. 4 in accordance with a preferred exemplary embodiment of the present invention.
Figure 6:
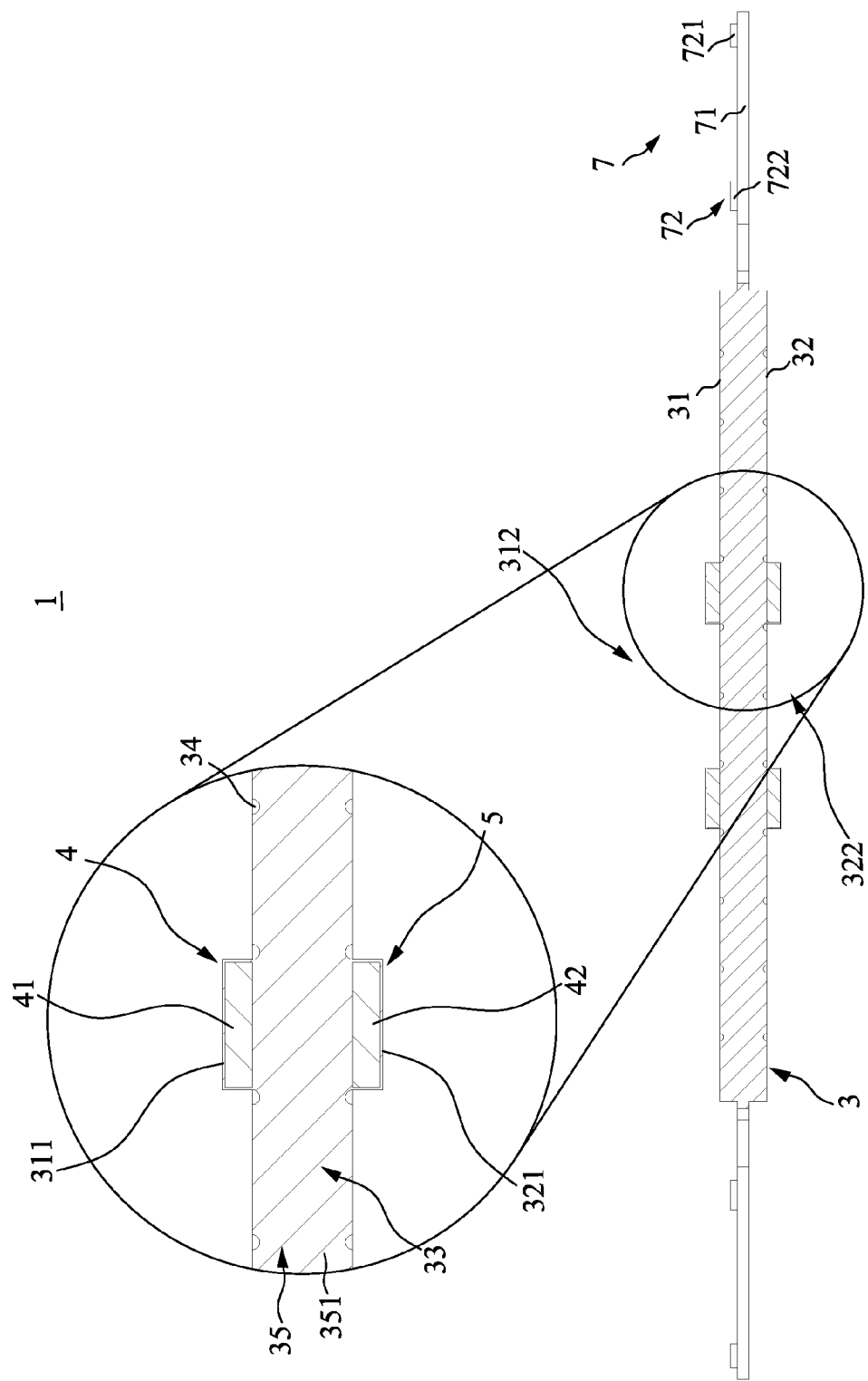
FIG. 6 is a cross-sectional schematic diagram illustrating a deformation body of the magnetic induction pad in accordance with a preferred exemplary embodiment of the present invention.

In accordance with FIGS. 4, 5 and 6, the deformation body 3 may have a first surface 31 and a second surface 32 that are in close connection with each other; and a filling space 33 is formed collectively by the inner surfaces of the first surface 31 and the second surface 32, and the fluid delivery device 6 may refill fluid into the filling space 33.

To be more precise, in accordance with a preferred exemplary embodiment of the present invention, a plurality mutually spaced and arranged joint lines 34 that have the appearance of straight lines are on the first surface 31 and the second surface 32 of the deformation body 3, whereby the straight lines are formed by the method of high frequency embossing. The filling space 33 may correspond to the plurality of joint lines 34, and a plurality of mutually arranged and spaced channels 35 may be formed. The plurality of joint lines may be configured to appear as a first channel 351, which is in a strip-like state. When the fluid is being refilled by the fluid delivery device 6, the first channel 351 of the deformation body 3 may be used for fast and continuous refilling to be achieved.

In addition to the above, in accordance with a preferred exemplary embodiment of the present invention, the edge of the outer surface of the first surface 31 and the second surface 32 may respectively form the two strengthening pieces 37 that may correspond to the conductive positions in between the first channel 351. The strengthening piece 37 includes a first anti-fold section 371 that is parallel to the edge position and a second anti-fold section 372 that is perpendicular to the first anti-fold section 371. The strengthening piece 37 is designed in a manner such that deformation amounts in different directions are produced by the edge region and central region of the deformation body 3 when the edge region and the central region are compressed. In other words, the strengthening piece 37 may enable the smooth conduction of the first channel 351, and also preventing recesses from occurring, caused by the compression of the bed body 2 as a result of the person lying on the bed. Furthermore, blockade of the filling space 33 may also be prevented.

In addition, two of the plurality of mutually spaced and arranged first bag bodies 311 exist in between the plurality of joint lines 34 of the first surface 31 of the deformation body 3; and two of the plurality of second bag bodies 321 that are mutually spaced and arranged exist in the corresponding position of the plurality of first bag bodies 311 on the second surface 32. The plurality of magnetic induction modules 4 are housed and also fixed by the plurality of first bag bodies 311 and the plurality of second bag bodies 321. In accordance with the present invention, the plurality of magnetic induction modules 4 are collectively made up of the group of magnetic members 41 of the plurality of first bag bodies 311 on the first surface 31 and the group of induction members 42 of the plurality of second bag bodies 321 of the second surface 32. The group of induction members 42 is in electrical connection with the processor 8 by means of a plurality of transmission lines 43. The plurality of transmission lines 43 are grouped by an endurance panel 44 (a PC board); and moreover, the plurality of transmission lines 43 also pass through the endurance panel 44. In accordance with this, the plurality of first bag bodies 311 on the first surface 31 are located at a corresponding location to the plurality of second bag bodies 321 on the second surface 32. This arrangement enables the group of magnetic members 41 and the group of induction members 42 to mutually induce each other in order to produce a magnetic force; the magnetic force is then converted to either voltage or current. In addition, the size of each of the plurality of first bag bodies 311 and the size of each of the plurality of second bag bodies 321 are almost the same as the size of each of the plurality of magnetic induction modules 4, in order to prevent the displacement of each of the plurality of magnetic induction modules 4 and as such, the group of magnetic members 41 and the group of induction members 42 would be unable to induce one another.

Furthermore, the strength of the magnetic force produced by the mutual induction between the group of magnetic members 41 and the group of induction members 42 is related to the deformation distance being long or short, which is caused by the compression of the filling space 33 of the deformation body 3 as a result of the person lying down on the bed body 2. In accordance with a preferred embodiment of the present invention, when the human body does not lie-down on the bed body 2, the magnetic induction pad 1 of the present invention does not receive the compression brought about by the weight of the human body, and no magnetic force would be induced between the group of magnetic members 41 and the group of induction members 42. Or when there is a magnetic force, the strength of the magnetic force would be very weak. When the human body lies down on the bed body 2, the magnetic induction 1 of the present invention is being compressed as a result of the weight of the human body, and a relatively strong magnetic force will be induced in between the group of magnetic members 41 and the group of induction members 42. However, when the human body suddenly turns over, or falls off the bed body 2, the magnetic force that is induced between the group of magnetic members 41 and the group of induction members 42 will decrease and will immediately become weak, and as such enabling one to determine whether the human body is still on the bed body 2.

Also referring to FIGS. 4, 5 and 6, the magnetic induction pad 1 of the present invention may collectively form a first pattern 312 on the first surface 31 and a second pattern 322 on the second surface 32 by means of the plurality of first and second bag bodies 311 and 321 on the outer surface of the deformation body 3. The plurality of first patterns 312 and the plurality of second patterns 322 may correspond to each other and may have the same pattern. As such, the positions of the plurality of first bag bodies 311 on the first surface 31 may be configured to be opposite to the positions of the plurality of second bag bodies 321 of the second surface 32. However, in accordance with the first preferred exemplary embodiment of the present invention, the plurality of first patterns 312 and the plurality of the second pattern 322 may be configured such that they may be mutually spaced and arranged pattern.

Furthermore, most of the surfaces of the magnetic induction pad 1 of the present invention may be covered by a coated piece 5. The coated piece 5 may be configured to include a coated body 51 that is a cover space. The coated body 51 may be configured to include a first cover member 511 that covers the first surface 31, a second cover member 512 that covers the second surface 32 and a third cover member 513 that is in connection with the first cover member 511 and the second cover member 512. An extension member 52 may be integrally extended from the third cover member 513. In addition to the extension member 52 and the third cover member 513, the other three sides of the coated body 51 may form an opening mode. The four corners of the coated body 51 may be configured to correspond to the plurality of gaps of the magnetic induction pad 1 that are located in the four corners of the magnetic induction pad 1, such that the four corners of the magnetic induction pad 1 may be exposed to outside of the magnetic induction pad 1. In addition, an acceleration sensing device 54 may be placed at the end of the extension member 52 that is far away from the coated body 51.

Also referring to FIGS. 4, 5 and 6, in accordance with a preferred exemplary embodiment of the present invention, it should be noted that the four corners of the magnetic induction pad 1 may be exposed to the corresponding four gaps 53 of the coated piece 5. In other words, the four corners of the magnetic induction pad 1 may be seen through the four gaps 53 of the coated piece 5. In addition, in order to enable the magnetic induction pad 1 to easily be in connection with the fluid delivery device 6, the gas nozzle 36 may be exposed to the outside of the coated piece 5 through one of the four gaps 53, and the four positioning belts 71 may be extended from the four gaps 53 of the coated piece 5.

Moreover, as shown in FIG. 6, the four corners the deformation body 3 may correspond to the connection parts between the first surface 31 and the second surface 32 that is opposite to the first surface 31, so as to form a positioning device 7. The positioning device 7 may be configured by a plurality of positioning belts 71 that correspond to a plurality of gaps 53. Each of the plurality of positioning belts 71 may be configured to include a pair of connection members 72 that may be mutually engaged. The pair of connection members 72 may include a male connection member 721 and a female connection member 722 on two opposite ends of each of the plurality of positioning belts 71. Two bedsides of the bed body 2 may be configured to include the plurality of positioning holes 25 that correspond to the positions of the plurality of positioning belts 71. Each of the plurality of positioning belts 71 may be penetrated into the corresponding one of the plurality of positioning holes 71 of the bed body 2, and then may be penetrated into another one of the plurality of positioning holes 71. In other words, the male connection member 721 of one of the plurality of positioning belts 71 may be engaged with the female connection member 722 of another one of the plurality of positioning belts 71. It should be ensured that the magnetic induction pad 1 of the present invention may be configured for a predetermined position of the bed body 2, such that the magnetic induction pad 1 that is placed on the bed body 2 may be not displaced.

In accordance with the preferred exemplary embodiment of the connection members, the present invention is not limited to the design of the connection members. The connection members that have the engaging and positioning effects may fall within the scope of the connection members of the present invention. Moreover, the pair of connection members 72 may be configured as a pair of male connection members or a pair of female connection members.

Figure 7:
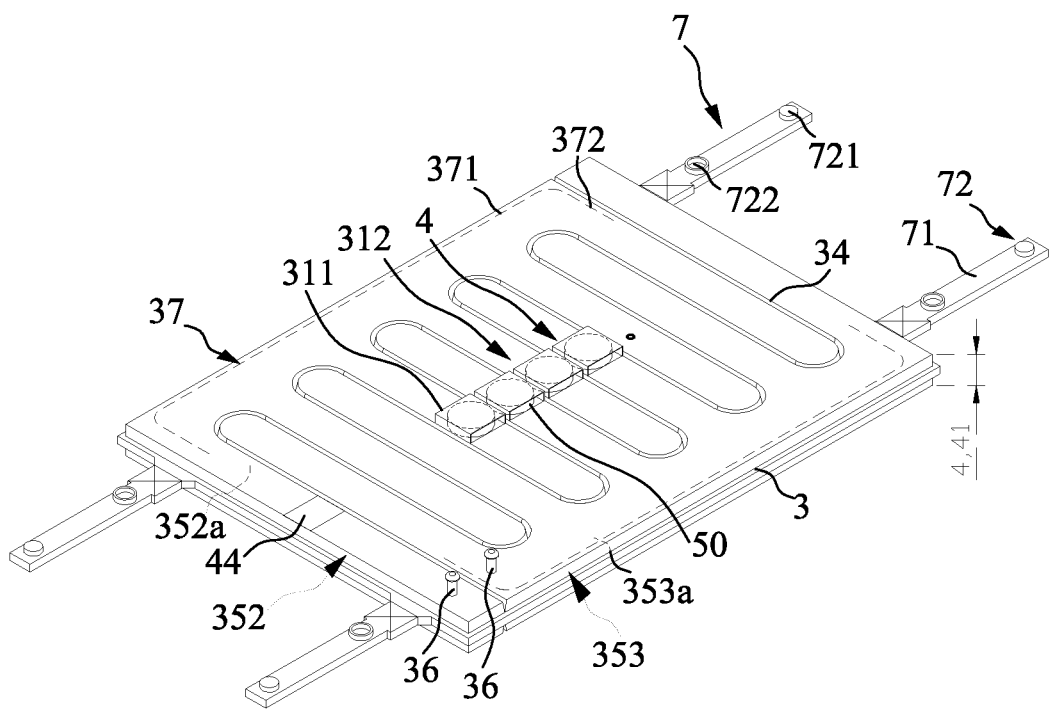
FIG. 7 is a three-dimensional schematic diagram illustrating a bag body of the magnetic induction pad in accordance with a second preferred exemplary embodiment of the present invention.

As shown in FIG. 7, and in accordance with a second preferred exemplary embodiment of the present invention, the second preferred exemplary embodiment of the present invention may be distinguished from the first preferred exemplary embodiment of the present invention by the following technical features. Firstly, a continuous curved-like pattern formed on the outer surface of the deformation body 3 may be formed by a high frequency wave printing manner.

Secondly, the filling space 33 may correspond to a first space 352 and a second space 353 that is adjacent to the first space 352, and the first space 352 and the second space 353 may be separated by the joint line 34. The first space 352 and the second space 353 may not be connected and may not have conduction. Accordingly, a pair of gas nozzles 36 may be configured on the outer surface of the deformation body 3; that is, one of the pair of gas nozzles 36 may be configured to be placed on the first space 352, and another one of the pair of gas nozzles 36 may be configured to be placed on the second space 353. The first space 352 may be connected to the second space 353 by the pair of gas nozzles 36. The first space 352 may have a plurality of second channels 352a that are parallel to each other, and the plurality of second channels 352 may be mutually connected by the ends of the plurality of second channels 352. In addition, the second space 353 may have a plurality of third channels 353a that are parallel to each other, and the plurality of third channels 353 may be mutually connected to each other by the ends of the plurality of third channels 353. Moreover, the plurality of second channels 352a and the plurality of third channels 353a may be arranged in an alternate manner. The outer surfaces of the first surface 31 and the second surface 32 may form two strengthening pieces 37 that correspond to the first space 352 and the second space 353, respectively. As such, it can be ensured that the first space 352 and the second space 353 may have smooth conduction by using the two strengthening pieces 37.

Thirdly, the outer surface of the first surface 31 and the outer surface of the second surface 32 may respectively form a first pattern 312 and a second pattern 322 as a continuous line pattern. The plurality of first bag bodies 311 of the first surface 31 and the plurality of second bag bodies 321 of the second surface 32 may be arranged and spaced continuously. The other parts of the second preferred exemplary embodiment of the present invention may be the same as those of the first preferred exemplary embodiment of the present invention. As such, they may no longer be repeated here.

Figure 8:
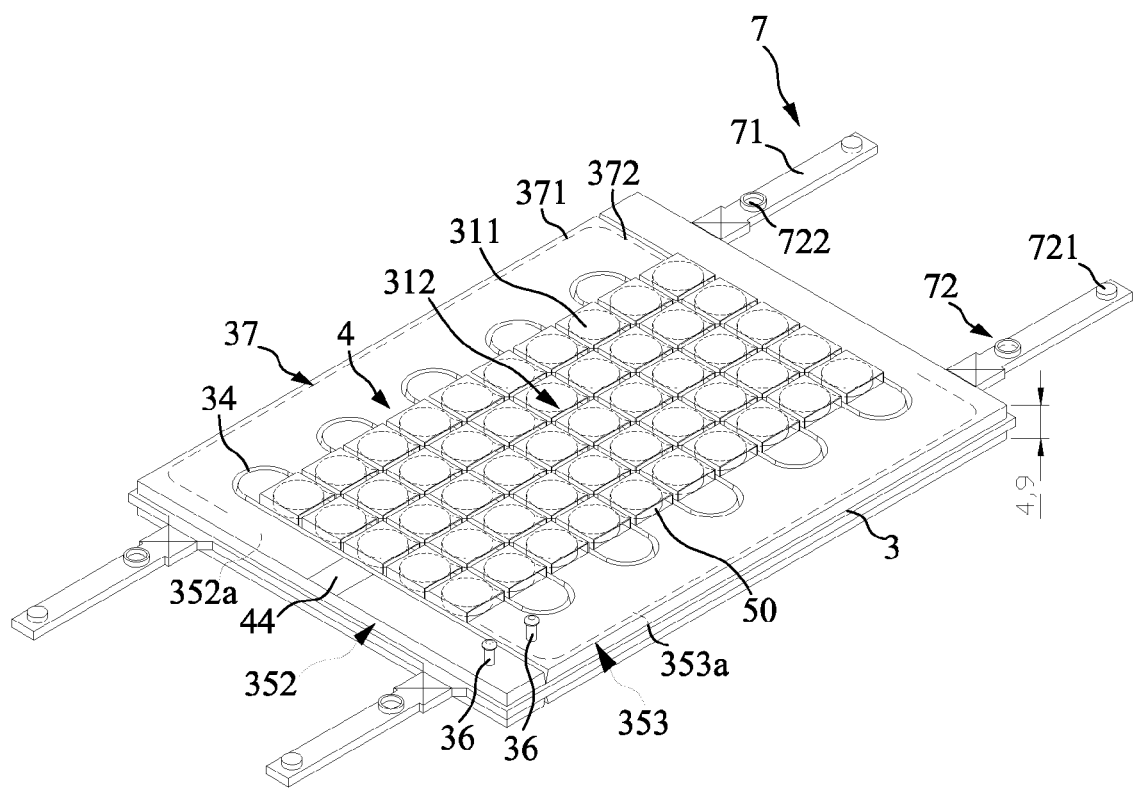
FIG. 8 is a schematic diagram illustrating a bag body of the magnetic induction pad in accordance with a third preferred exemplary embodiment of the present invention.

As shown in FIG. 8, in accordance with the third preferred exemplary embodiment of the present invention may be distinguished from the second preferred exemplary embodiment of the present invention by the plurality of first patterns 312 and the plurality of second patterns 322 that are formed respectively on the outer surface of the first surface 31 and the outer surface of the second surface 32 as a continuous spaced and arranged checkerboard pattern. Therefore, the checkerboard pattern may be distributed on most of the outer surface of the first surface 31 and most of the outer surface of the second surface 32. The other parts of the third preferred exemplary embodiment of the present invention may be the same as those of the second preferred exemplary embodiment of the present invention. As such, they may no longer be repeated here.

Figure 9:
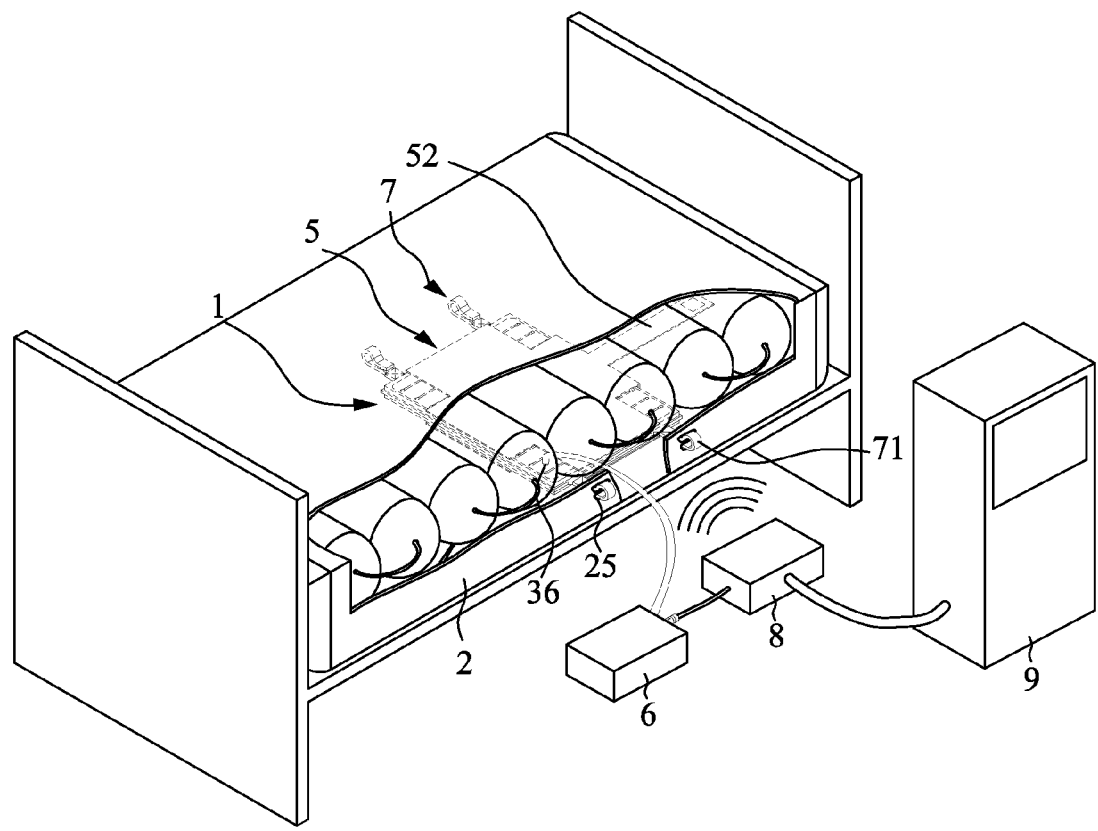
FIG. 9 is three-dimensional schematic diagram illustrating the magnetic induction pad that is in connection with a plurality of magnetic induction modules and a processor via wireless transmission in accordance with a preferred exemplary embodiment of the present invention.

As shown in FIG. 9, the group of induction members 42 of the plurality of magnetic induction modules 4 of FIG. 2 is in connection with the processor 8 via a plurality of transmission lines 43. However, according to another preferred exemplary embodiment of the present invention, the group of induction members 42 of the plurality of magnetic induction modules 4 may be in connection with the processor 8 via a wireless connection to enable an induction connection to be conducted.

Figure 10:
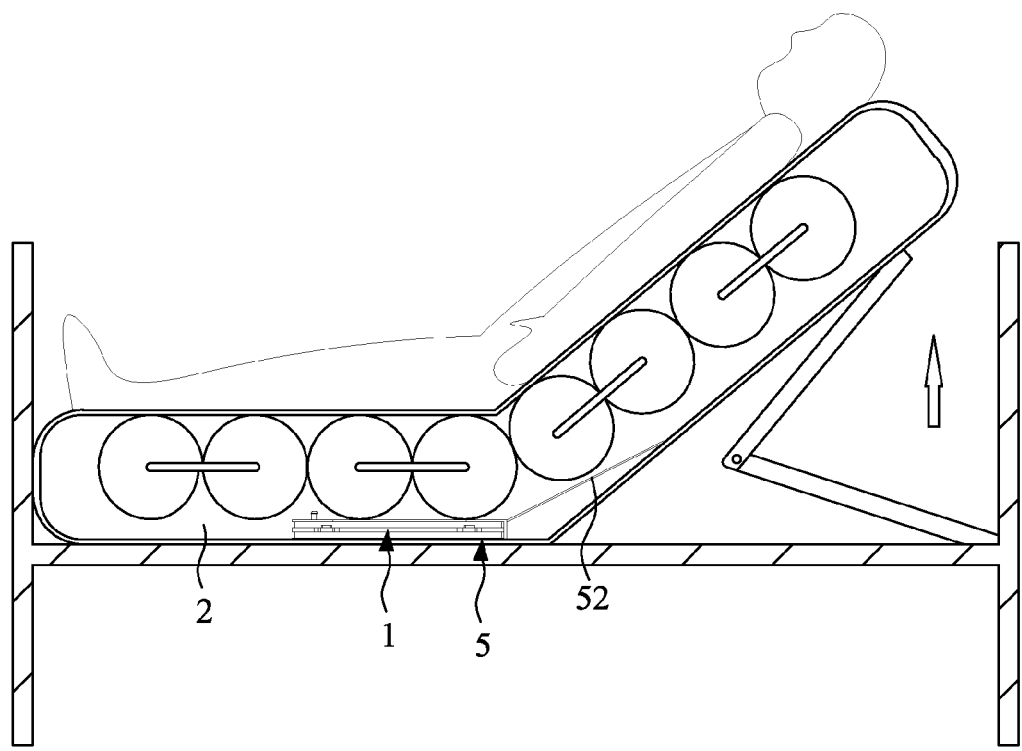
FIG. 10 is a schematic diagram illustrating the magnetic induction pad when the head part of the bed is raised in accordance with a preferred exemplary embodiment of the present invention.

Finally, as shown in FIG. 10, the acceleration sensing device 54 may be placed in the interior of the bed body 2 and below the air bag, and may be located approximately in the position of the upper body area 22. Accordingly, when the upper body area 22 is raised, the body weight of the buttock part area 23 may concentrate in the area above the magnetic induction pad 1 of the present invention. As such, the magnetic induction pad 1 of the present invention may sense the upper body area 22 via the acceleration sensing device 54, and may subsequently transmit information to the processor 8. The processor 8 may send an instruction to the fluid delivery device 6 to enable the filling space 33 to be filled with fluids. The deformation distance of the deformation body 3 that is excessively large may be avoided. In other words, a certain sensing space between the group of magnetic member 41 and the group of induction members 42 may be maintained.

Although the preferred exemplary embodiments of the present invention have been described with reference to the preferred exemplary embodiments thereof, it may be apparent to those ordinarily skilled in the art that a variety of modifications and changes may be made without departing from the scope of the present invention which is intended to be defined by the appended claims.

What is claimed is:

1. A magnetic induction pad with bed leaving sensing function, comprising:
   a deformation body, wherein the interior of the deformation body comprises a filling space that enable the deformation body to change the volume and size; wherein the filling space is in connection with the outside via at least one gas nozzle, the external of the deformation body comprises a first surface and a second surface; the first surface comprises a plurality of first bag bodies, and the second surface comprises a plurality of second bag bodies, wherein the plurality of first bag bodies are mutually arranged to form a first pattern, and the plurality of second bag bodies are mutually arranged to form a second pattern that is the same as the first pattern, so as to enable the position of each of the plurality of first bag bodies on the first surface to have a corresponding arrangement to each of the plurality of second bag bodies on the second surface; and
   a plurality of magnetic induction modules, wherein the plurality of magnetic induction modules comprise a group of magnetic members and a group of induction members, the group of magnetic members and the group of induction members are respectively arranged at the corresponding positions within the plurality of first bag bodies and the plurality of second bag bodies, and wherein the group of magnetic members and the group of induction members are used for sensing any changes in the distance of the first surface relative to the second surface.

2. The magnetic induction pad in accordance with claim 1, wherein the first surface and the second surface further comprise a plurality of joint lines that are mutually parallel, so as to enable the filling space to form a plurality of channels, and conduction exists in between the plurality of channels.

3. The magnetic induction pad in accordance with claim 2, wherein the filling space comprises a plurality of first channels that are parallel, adjacent and in connection with each other.

4. The magnetic induction pad in accordance with claim 2, wherein the filling space comprises a first space and a second space that are not in connection with each other; the first space comprises a plurality of second channels that are parallel to each other, and the plurality of second channels are in connection with each other via the terminal regions; a third space comprises a plurality of third channels that are parallel to each other, and the plurality of third channels are in connection with each other via the terminal regions; and the plurality of second channels and the plurality of third channels have a sequential alternating arrangement.

5. The magnetic induction pad in accordance with claim 1, wherein an edge of at least one of the first surface and the second surface comprises at least one strengthening piece, so as to enable an edge region and the central region of the deformation body to respectively produce deformations in different directions when the deformation body is being compressed.

6. The magnetic induction pad in accordance with claim 5, wherein the at least one strengthening piece comprises a first anti-fold section and a second anti-fold section, wherein the first anti-fold section is parallel to the edge position, and wherein the second anti-fold section is perpendicular to the first anti-fold section.

7. The magnetic induction pad in accordance with claim 1, wherein the plurality of magnetic induction modules further comprises a processor, wherein the processor is electrically connected to the group of induction members and a fluid delivery device, and wherein the fluid delivery device is in connection with the gas nozzle of the deformation body, and wherein the fluid delivery device selectively inputs a filling material to the filling space of the deformation body to change the volume of the filling space.

8. The magnetic induction pad in accordance with claim 1, wherein two opposite sides of the magnetic induction pad further comprises a positioning device, and wherein the positioning device comprises a plurality of positioning belts that are in connection with the external edge of the deformation body, and wherein the positioning belt comprises a group of connection members.

9. The magnetic induction pad in accordance with claim 8, wherein each connection member comprises a male connection member and a female connection member, wherein the female connection member is adjacent to the male connection member; the male connection member is in connection with the female connection member to surround the positioning belt to form a positioning space that enables the bed to be positioned.

10. The magnetic induction pad in accordance with claim 1, wherein the magnetic induction pad further comprises a coated piece, wherein the coated piece comprises a coated body that forms a cover space, and an extension member is formed by the coated body extending outwards; and the cover space is used for covering the most part of surface of the deformation body, and wherein the extension member comprises an acceleration sensing device.

11. The magnetic induction pad in accordance with claim 10, wherein the coated body comprises a first cover member that covers the first surface, a second cover member that covers the second surface and a third cover member that is in connection with the first cover member and the second cover member; the extension member is integrally connected with the third cover member.

* * * * *